United States Patent
Kimock et al.

(10) Patent No.: US 10,413,696 B2
(45) Date of Patent: Sep. 17, 2019

(54) MEDICAL HEADGEAR

(71) Applicant: Neatcap, LLC, Bethlehem, PA (US)

(72) Inventors: Fred M. Kimock, Macungie, PA (US); Zachary Rambo, Sellersville, PA (US); Benjamin J. Kimock, Macungie, PA (US); Andrew Unger, Emmaus, PA (US); Edward G. Thear, Kure Beach, NC (US); Gayle H. Thear, Kure Beach, NC (US)

(73) Assignee: Neatcap, LLC, Bethlehem, PA (US)

( * ) Notice: Subject to any disclaimer, the term of this patent is extended or adjusted under 35 U.S.C. 154(b) by 572 days.

(21) Appl. No.: 14/626,325

(22) Filed: Feb. 19, 2015

(65) Prior Publication Data

US 2016/0243327 A1    Aug. 25, 2016

(51) Int. Cl.
| | |
|---|---|
| *A61M 16/06* | (2006.01) |
| *A61F 11/14* | (2006.01) |
| *A61F 11/06* | (2006.01) |
| *G10K 11/00* | (2006.01) |
| *A61F 13/12* | (2006.01) |
| *G10K 11/16* | (2006.01) |

(52) U.S. Cl.
CPC ......... *A61M 16/0683* (2013.01); *A61F 11/06* (2013.01); *A61F 11/14* (2013.01); *A61M 16/0672* (2014.02); *A61F 13/12* (2013.01); *A61M 16/0644* (2014.02); *A61M 2205/0216* (2013.01); *A61M 2205/42* (2013.01); *G10K 11/002* (2013.01); *G10K 11/16* (2013.01)

(58) Field of Classification Search
CPC .......... A61F 11/06; A61F 11/08; A61F 11/10; A61F 11/12; A61F 11/14; A61F 9/029; A61F 13/12; A61F 2011/085; A61F 2011/145; A42B 1/068; A42B 1/245; G10K 11/002; G10K 11/16; G10K 11/162; G10K 11/168; G10K 11/172; G10K 11/175; A61M 16/0683; A61M 16/0672; A61M 16/0644
USPC ...... 128/864, 865, 866, 867, 868; 2/11, 209, 2/171, 181, 909, 918, DIG. 11, 183, 205; 181/128, 129; 381/370, 371, 372, 374, 381/376, 71.71, 71.6, 71.7; 602/74
See application file for complete search history.

(56) References Cited

U.S. PATENT DOCUMENTS

| | | | |
|---|---|---|---|
| 1,489,145 A | 4/1924 | O'Keefe | |
| 3,875,592 A | 4/1975 | Aileo | |
| 4,037,273 A * | 7/1977 | Labaire | A61F 11/14 2/209 |
| 4,802,245 A | 2/1989 | Miano | |
| 4,805,239 A | 2/1989 | Ciago | |
| 4,830,138 A | 5/1989 | Palmaer et al. | |
| 4,907,576 A * | 3/1990 | Curlee | A61F 5/028 602/19 |
| 5,038,412 A | 8/1991 | Cionni | |

(Continued)

FOREIGN PATENT DOCUMENTS

BR    PI0403859-2 B1    11/2010

*Primary Examiner* — Keri J Nelson
(74) *Attorney, Agent, or Firm* — Barley Snyder

(57) ABSTRACT

A medical headgear is disclosed having a flexible band having an inner surface and an opposite outer surface. The band includes a non-stretch central portion having a first side and an opposite second side, a first elastic portion connected to the first side, and a second elastic portion connected to the second side.

38 Claims, 11 Drawing Sheets

(56) References Cited

U.S. PATENT DOCUMENTS

| | | | |
|---|---|---|---|
| 5,058,606 A * | 10/1991 | Malkoff | A61F 11/06 128/864 |
| 5,188,101 A * | 2/1993 | Tumolo | A61M 25/02 128/101.1 |
| 5,243,709 A * | 9/1993 | Sheehan | A61F 11/14 2/209 |
| 5,420,381 A * | 5/1995 | Gardner, Jr. | A61F 11/14 181/129 |
| 5,713,078 A | 2/1998 | DeAngelis | |
| 5,887,286 A | 3/1999 | Waldron | |
| 6,126,683 A * | 10/2000 | Momtaheni | A61F 5/34 602/13 |
| 6,269,488 B1 * | 8/2001 | Jurgensen | A45D 8/00 132/273 |
| 7,878,968 B2 | 2/2011 | Wittmann-Price et al. | |
| 8,526,658 B1 | 9/2013 | Houston | |
| 8,534,290 B2 | 9/2013 | Karrman | |
| 2004/0221370 A1 * | 11/2004 | Hannula | A41D 20/00 2/181 |
| 2007/0044206 A1 * | 3/2007 | Sato | A61F 11/14 2/209 |
| 2007/0235034 A1 * | 10/2007 | Weaver | A61M 16/0666 128/207.18 |
| 2008/0264715 A1 * | 10/2008 | Leong | A61F 11/08 181/135 |
| 2009/0178177 A1 * | 7/2009 | Fairclough | A42B 1/068 2/209 |
| 2009/0205900 A1 * | 8/2009 | Purcell | A61F 11/14 181/129 |
| 2009/0260134 A1 * | 10/2009 | Wittmann-Price | A42B 1/245 2/423 |
| 2012/0012418 A1 * | 1/2012 | Nilsson | A61F 11/14 181/126 |
| 2012/0210497 A1 * | 8/2012 | Rodarmel | A41D 27/08 2/244 |
| 2013/0133671 A1 * | 5/2013 | Fairclough | A42B 1/068 128/866 |
| 2014/0003614 A1 | 1/2014 | Levitov et al. | |

* cited by examiner

MEDICAL HEADGEAR

FIELD OF THE INVENTION

The invention generally relates to headgear, and more specifically to a medical headgear.

BACKGROUND

Approximately twelve percent of newborns are born preterm in the U.S. These preterm newborns frequently require long, expensive, and stressful hospital stays in neonatal intensive care units (NICUs), and present a number of unique challenges. Studies have shown that the total brain weight achieved at 34 weeks can be as little as 65% of that of a full term newborn, with the remaining brain development occurring outside the protection of the utero environment. Further studies have shown that preterm newborns exhibit decreased cerebral cortex volume and cerebellar growth when compared to their full term counterparts, frequently emerging from NICUs having developmental and neurosensory deficits.

Advances in preterm newborn developmental research suggest that the loud, atypical acoustic environments characteristic of NICUs may contribute to the decreased cerebral cortex volume and cerebellar growth, resulting in negative outcomes involving hearing, growth, and ultimately, cognition. Exposure of preterm newborns to environmental stimuli that do not correspond to the normal in-utero acoustic environment induces stress, which negatively impacts sleep, growth, and sensory development processes. The negative impact is thought to disrupt and alter normal brain development in response to the external environmental stimuli.

Generally, a mother's body and amniotic fluid surround a developing fetus, providing a natural acoustic filter, with sound attenuation increasing as a function of frequency. The gravid uterus plus amniotic fluid provides negligible sound attenuation of frequencies less than about 300 Hz, then sound attenuation increases monotonically up to 15-20 decibels (dB) at about 2,000 Hz. Above 2,000 Hz, the gravid uterus effectively blocks sound, i.e. attenuation is 15-20 dB or greater.

Attempts have been made to adapt NICUs to reduce the environmental noise levels, including the installation of low-noise incubation equipment and sound-absorbing materials in floors, walls, and ceilings. Other attempts include the use of single-bed NICU rooms to allow better control of the environmental noise levels. While these approaches do reduce some environmental noise, they are only marginally effective, and are often cost prohibitive for many institutions.

Further attempts to reduce environmental noise include the use of foam earcups that are placed over the ears of a preterm newborn, and attached through the use of an adhesive. While the foam earcups do provide limited sound attenuation, the filtered sound profile does not correspond to the normal in-utero acoustic environment. As a result, the effectiveness of the foam earcups is extremely limited.

Another unique challenge with preterm newborns is that their skin and facial features are very delicate and extremely susceptible to damage, such as tearing. This presents several problems for implementation of devices to support development.

Firstly, the foam earcups rely on a hydrogel adhesive to bond the earcup to the skin to form an acoustic seal. The hydrogel adhesive is very sensitive to conditions of application. If the foam ear cup is very lightly positioned, in order to prevent damage to the skin, the adhesive bond is very weak, and the bond between the earcups and the skin of the preterm newborn fails within a few hours. In other instances, the adhesive bond to the skin is too strong, and extreme care must be taken when peeling the bonded earcup away from the skin to remove the foam earcup. Often, the removal process results in damage to the skin, such as tearing or irritation.

Secondly, the underdeveloped lungs in preterm newborns frequently require respiratory support in the form of conventional mechanical ventilation, high frequency ventilation, or continuous positive airway pressure (CPAP) delivered through respiratory support tubes positioned in the oral cavity or nose by a nasal cannula. While there are many conventional respiratory support tube attachment devices available for full-term newborns and adults, these devices are not suited for the delicate skin or nasal septum of preterm newborns. Consequently, the respiratory support tubes are commonly attached to fabric caps by safety pins and rubber bands, or directly to the skin of the preterm newborn by medical tape. Extreme care must be taken during removal of the medical tape, to avoid injury to the preterm newborn.

Consequently, there is a strong need for a medical headgear that is suitable for use on preterm newborns, that reduces environmental noise to in-utero acoustic levels, and provides a stable support for attaching respiratory support tubes and other medical devices.

SUMMARY

A medical headgear has a flexible band with an inner surface and an opposite outer surface. The band includes a non-stretch central portion having a first side and an opposite second side, a first elastic portion connected to the first side, and a second elastic portion connected to the second side.

BRIEF DESCRIPTION OF THE DRAWINGS

The invention will now be described by way of example with reference to the accompanying figures, of which.

DETAILED DESCRIPTION

Figure 1:
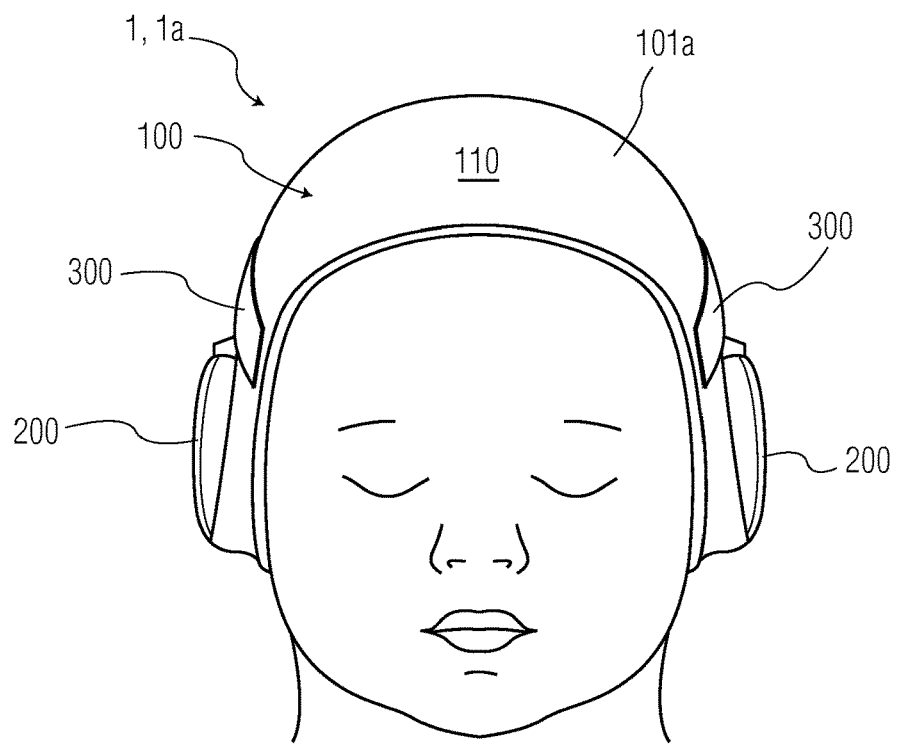
FIG. 1 is a front perspective view of a rear-closing medical headgear installed on a head of a preterm newborn.

In the embodiments of FIGS. 1-17, a medical headgear 1 has a flexible band 100, a pair of earcups 200, and a plurality of medical device fasteners 300.

The flexible band 100 is elongated, extending along a longitudinal axis, having an outer surface 101a and an inner surface 101b. The flexible band 100 includes a non-stretch central portion 110, a first elastic portion 120, a second elastic portion 130, a first non-stretch terminating end portion 140, and a second non-stretch terminating end portion 150.

In an embodiment, the flexible band 100 is formed from a continuous length of a single layer of material of a suitable biocompatible natural or synthetic elastic material, such as neoprene rubber, styrene-butadiene rubber, neoprene-styrene-butadiene composite rubber, polyurethane, nylon, spandex, nylon-spandex blend, polyesters, polyamides, cotton-spandex blend, or a combination thereof. In an embodiment, the flexible band 100 is formed from a continuous length of two or more layers of elastic band materials having a core comprising neoprene rubber, styrene-butadiene rubber, neoprene-styrene-butadiene composite rubber, or polyurethane, with a layer of nylon or nylon-spandex laminated onto the outer surface 101a, the inner surface 101b, or both surfaces 101a,101b.

In an embodiment, non-stretch portions of the flexible band 100 are formed from woven fabrics that impart the non-stretch physical characteristic. In an embodiment, the stretch or elastic portions of the flexible band 100 are formed from non-woven fabrics, knitted fabrics, or woven fabrics containing spandex that individually or when combined with a suitable core material impart the stretch or elastic physical characteristic.

In an embodiment, the flexible band 100 is made from a plurality of fabric segments mechanically fastened together through common methods such as stitching or adhesive. For example, the non-stretch central portion 110 and the first and second non-stretch terminating end portions 140,150 may be formed from a first non-stretch material, and the first and second elastic portions 120,130 may be formed from an elastic material.

The non-stretch central portion 110 has a first end (not labeled) and an opposite second end (not labeled). A first friction pad 111a positioned on the inner surface 101b, between the first and second ends. The first friction pad 111a is formed from a grip or tacky material, such as silicone. In an embodiment, the first friction pad 111a is mechanically or chemically attached to the inner surface 101b by an adhesive or stitching.

In an embodiment, the first friction pad 111a is formed from a thin, generally rectangular sheet of silicone rubber. In another embodiment, the first friction pad 111a includes a single longitudinal stripe, multiple longitudinal or vertical stripes, dots, or other patterns, formed by known painting, printing, or spray processes, which chemically or mechanically adheres the first friction pad 111a to the inner surface 101b.

Figure 6:
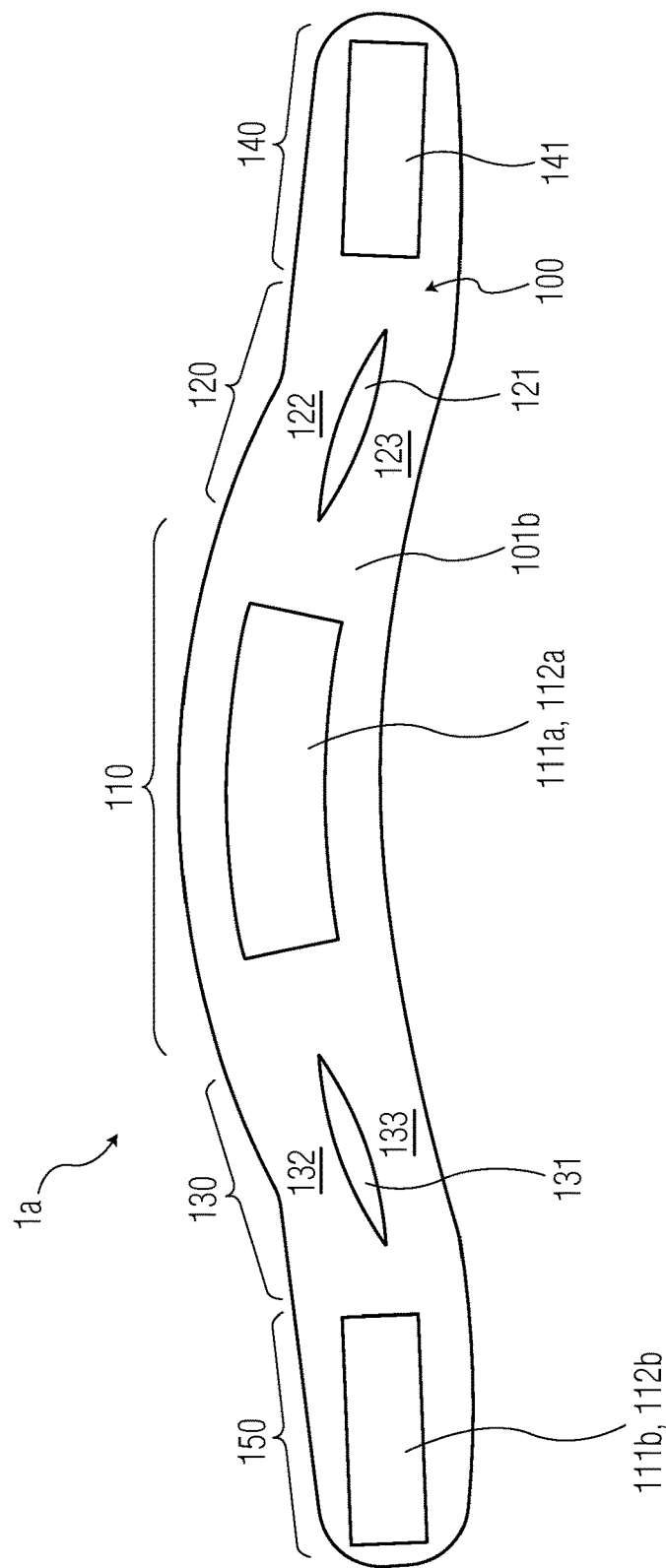
FIG. 6 is a perspective view of an inner facing side of the rear-closing medical headgear.

In an embodiment of FIG. 6, a first non-stretch pad 112a is optionally positioned on the inner surface 101b of the non-stretch central portion 110. The first non-stretch pad 112a is formed from a non-stretch material such as microfiber, or other woven fabrics, which may impart the non-stretch physical property to the non-stretch central portion 110. The first non-stretch pad 112a may be mechanically or chemically attached to the inner surface 101b by stitching or an adhesive.

In an embodiment, the first friction pad 111a is positioned on an outer surface of the first non-stretch pad 112a.

In an embodiment of FIG. 6, a length of the non-stretch central portion 110 is proportional to a length of the first friction pad 111a and/or first non-stretch pad 112a, such that increasing the length of the first friction pad 111a and/or the first non-stretch pad 112a increases the length of the non-stretch central portion 110. Conversely, decreasing the length of the first friction pad 111a and/or the first non-stretch pad 112a decreases the length of the non-stretch central portion 110. In another embodiment, the non-stretching physical properties and length of the central portion 110 are controlled through at least one or more rows of longitudinally extending stitching (not shown), which prevent elastic stretching along the longitudinal axis. In another embodiment, the non-stretching central portion 110 is formed from the first non-stretch material.

In another embodiment, the central portion 110 is made of an elastic material, and therefore stretches under an applied circumferential tensile force across the band. Optionally, the first pad 112a may also be formed from an elastic material, allowing the central portion 110 to maintain elasticity in the presence of the first pad 112a.

The first elastic portion 120 has a terminating end connecting side, and an opposite central portion connecting side extending continuously from the first side of the non-stretch central portion 110 along the longitudinal axis. In an embodiment, when the first elastic portion 120 is formed from the elastic material and the non-stretch central portion 110 is formed from the first non-stretch material, the central portion connecting side of the first elastic portion 120 is mechanically connected to the first side of the non-stretch central portion 110 through an adhesive or stitching.

In an embodiment, the first elastic portion 120 is bifurcated, having a first earcup receiving space 121 positioned along an approximate middle section, an upper strap 122, and a corresponding lower strap 123. The first earcup receiving space 121 is defined by the upper strap 122 and the lower strap 123, having an elastically expandable first diameter. In an embodiment, the first earcup receiving space 121 is a slit extending for a distance along the longitudinal axis and passing through the band 100, and positioned between the upper strap 122 and lower strap 123. In an embodiment, a width of the upper strap 122 and a width of the lower strap 123 are equal. In another embodiment, the widths of the upper strap 122 and lower strap 123 are different. In another embodiment each strap 122,123 displays a unique elastic tension between the straps 122,123.

In an embodiment, the material of one or both of the straps 122,123 is gathered along a substantial mid-portion through a series of stitches (not shown), such that the elastic tension exerted by the straps 122,123 is controlled by the pattern, tightness, and length of stitching of the gathered material. For example, the use of a straight stitching pattern reduces the elastic tension, whereas a zig-zag stitching pattern can maintain the inherent elasticity of the flexible band 100 material. Additionally, the gathered material increases the unexpanded first diameter. Further, the gathered material may assist in retaining the earcups within the first receiving space 121.

In an embodiment, the second elastic portion 130 is complementary and substantially similar to the first elastic portion 120. The second elastic portion 130 has a terminating end connecting side, and a central portion connecting side extending continuously from the second side of the non-stretch central portion 110 along the longitudinal axis. Similar to the first elastic portion 130, in an embodiment, when the second elastic portion 130 is formed from the elastic material and the non-stretch central portion 110 is formed from the first non-stretch material, the central portion connecting side of the second elastic portion 130 is mechanically connected to the second side of the non-stretch central portion 110 through an adhesive or stitching.

The second elastic portion 130 is bifurcated, having a second earcup receiving space 131 positioned along an approximate middle section, an upper strap 132, and a corresponding lower strap 133. The second earcup receiving space 131 is defined by the upper strap 132 and the lower strap 133, having an expandable second diameter. In an embodiment, the second earcup receiving space 131 is a slit extending for a distance along the longitudinal axis and passing through the band 100, and positioned between the upper strap 132 and lower strap 133.

In an embodiment, a width of the upper strap 132 and a width of the lower strap 133 are equal. In another embodiment, the widths of the upper strap 132 and lower strap 133 are different. In another embodiment, each strap 132,133 displays a unique elastic tension between the straps 132,133.

In an embodiment, the material of one or both of the straps 132,133 is gathered along a substantial mid-portion through a series of stitches (not shown), such that the elastic tension exerted by the straps 132,133 is controlled by the pattern, tightness, and length of stitching of the gathered material. For example, the use of a straight stitching pattern reduces the elastic tension, whereas a zig-zag stitching pattern can maintain the inherent elasticity of the flexible band 100 material. Additionally, the gathered material increases the unexpanded second diameter. Further, the gathered material may assist in retaining the earcups within the second receiving space 131.

In an embodiment of FIG. 17, the first elastic portion 120 and second elastic portion 130 extend continuously as unbifurcated portions of fabric from the first side and second side of the central non-stretch portion 110 such that the portions 120,130 may completely cover and retain the earcup 200 (discussed in detail below). In an embodiment, the elastic tension of the first and second elastic portions 120,130 may be controlled by longitudinally extending stitching. Similar to the above-discussed bifurcated embodiments, the elastic tension may be controlled by the pattern, tightness, and length of the longitudinally extending stitching. For example, the use of a straight stitching pattern reduces the elastic tension, whereas a zig-zag stitching pattern can maintain the inherent elasticity of the flexible band 100 material.

In the embodiments of FIGS. 2-8, the first non-stretch terminating end portion 140 has an elastic portion connecting side extending continuously from the terminating end connecting side of the first elastic portion 120, and an opposite terminating end. The first non-stretch terminating end portion 140 includes a first fastener 141 positioned on the inner surface 101b. In another embodiment (not shown), the first fastener 141 is positioned on the outer surface 101a. When the first fastener 141 is positioned on the outer surface 101a, a friction pad (not shown) substantially similar to the first friction pad 111a, may also positioned on the inner surface 101b of the first non-stretch terminating end portion 140.

Attachment of the first fastener 141 imparts the non-stretching physical property to the first terminating end portion 140. A length of the first non-stretch terminating end portion 140 is proportional to a length of the first fastener 141, such that increasing the length of the first fastener 141 increases the length of the first non-stretch terminating end portion 140. Conversely, decreasing the length of the first fastener 141 decreases the length of the first non-stretch terminating end portion 140. Additionally, when the friction pad is positioned on the inner surface 101b, the non-stretching physical property is further enhanced.

In an embodiment, when the first non-stretch terminating end portion 140 is formed from a non-stretch material, the non-stretch material imparts the non-stretching physical property. In an embodiment, the first fastener 141 is a hook and loop style fastener, although one of ordinary skill in the art would appreciate that other common fasteners may be used.

In an embodiment, the first terminating end portion 140 is elastic, being formed from an elastic material similar to, or the same as, the elastic material forming the first elastic portion 120. In this embodiment, the first fastener 141 may also be elastic, such as a stretchable hook and loop style fastener.

In another embodiment, a first part of the first terminating end portion 140 is elastic, and a second part of the first terminating end portion 140 is non-stretch. The non-stretch second part may be non-stretch through the use of a non-stretch material, or controlled through the addition of the medical device fastener 300 on the outer surface 101a of the band 100, along the second part of the first terminating end portion 140.

In the embodiments of FIGS. 2-8, the second non-stretch terminating end portion 150 has an elastic portion connecting side extending continuously from the terminating end connecting side of the second elastic portion 130, and an opposite terminating end. In an embodiment, the second non-stretch terminating end portion 150 includes the second fastener 151 positioned on the outer surface 101a. When the second fastener 151 is positioned on the outer surface 101a, a second friction pad 111b, that may be optionally attached to a second non-stretch pad 112b, may be positioned on the inner surface 101b of the second non-stretch terminating end portion 150. In another embodiment (not shown), the second fastener 151 is positioned on the inner surface 101b. Similar to the above-discussed embodiments of the first non-stretch terminating end portion 140, attachment of the second fastener 151 imparts the non-stretching physical property to the second terminating end portion 150. A length of the second non-stretch terminating end portion 150 is proportional to a length of the second fastener 151, such that increasing the length of the second fastener 151 increases the length of the second non-stretch terminating end portion 150. Conversely, decreasing the length of the second fastener 151 also decreases the length of the second non-stretch terminating end portion 150. Additionally, when the second friction pad 111b is positioned on the inner surface 101b, the non-stretching physical property is further enhanced.

In an embodiment, when the second non-stretch terminating end portion 150 is formed from a non-stretch material, the non-stretch material imparts the non-stretching physical property.

In an embodiment, the second fastener 151 is a hook and loop style fastener complementary to the first fastener 141, although one of ordinary skill in the art would appreciate that other common fasteners may be used, so long as the first and second fasteners 141,151 are complementary.

In an embodiment, the second terminating end portion 150 is elastic, being formed from an elastic material similar to, or the same as, the elastic material forming the second elastic portion 130. In this embodiment, the first fastener 141 may also be elastic, such as a stretch hook and loop style fastener.

In another embodiment, a first part of the second terminating end portion 150 is elastic, and a second part of the second terminating end portion 150 is non-stretch. The non-stretch second part may be non-stretch through the use of a non-stretch material, or controlled through the addition of the medical device fastener 300 on the outer surface 101a of the band 100, along the second part of the second terminating end portion 150.

In an embodiment, the first fastener 141 is positioned on a surface opposite to that of the second fastener 151. For example, when the first fastener 141 is positioned on the inner surface 101b, the second fastener 151 is positioned on the outer surface 101a. Conversely, when the first fastener 141 is positioned on the outer surface 101b, the second fastener 151 is positioned on the inner surface 101a.

In an embodiment, the flexible band 100 extends linearly along the longitudinal axis. In another embodiment, the first and second non-stretch terminating end portions 140,150 extend along the longitudinal axis. The non-stretch central portion 110 and first and second elastic portions 120,130 taken together form an arcuate bend extending a distance from the longitudinal axis at an approximate mid-point.

The earcup 200 is a frequency-dependent auditory filter providing sound attenuation generally increasing as a function of frequency, with limited attenuation in the in-utero auditory range. In an embodiment, earcup 200 is a frequency-dependent auditory filter providing sound attenuation that approximates the sound attenuation characteristics of a mother's gravid uterus and abdominal cavity. In an embodiment, each earcup 200 provides at least 12 A-weighted decibels (dBA) of sound attenuation of pink noise. In another embodiment, each earcup 200 provides at least 15 dBA of sound attenuation of pink noise. In another embodiment, each earcup 200 provides at least 20 dBA of sound attenuation of pink noise.

In an embodiment, each earcup 200 provides at least an 8 decibel (dB) noise reduction rating (NRR) or more. In an embodiment, each earcup 200 provides an 8-12 dB NRR. In another embodiment, each earcup 200 provides a 9-11 dB NRR. In an embodiment, each earcup 200 provides at least a 10 dB NRR or more.

In an embodiment, each earcup 200 allows sound frequencies of 300 Hz or less to pass with attenuation less than 10 dB (SPL). In an embodiment, each earcup 200 allows sound frequencies of 400 Hz or less to pass with attenuation less than 10 dB (SPL). In another embodiment, each earcup 200 allows sound frequencies of 500 Hz or less to pass with attenuation less than 10 dB (SPL). In an embodiment, each earcup 200 is a frequency-dependent auditory filter attenuating sounds between 300-500 Hz. In another embodiment, each earcup 200 is a frequency-dependent auditory filter substantially blocking sounds above 2000 Hz. In an embodiment, "substantially blocking" is understood to be at least 98% (17 dB) or more. In another embodiment, "substantially blocking" is understood to be at least 99% (20 dB) or more.

Figure 10:
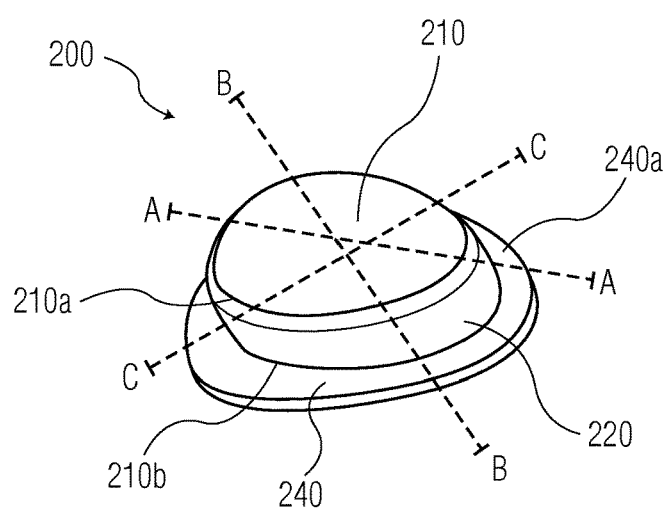
FIG. 10 is an oblique perspective view of an outer surface of the earcup.
Figure 11:
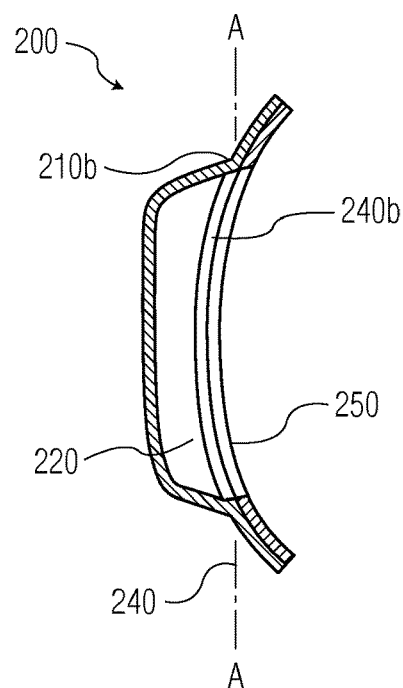
FIG. 11 is a cross-sectional view of the earcup along an A-A line of FIG. 10.
Figure 12:
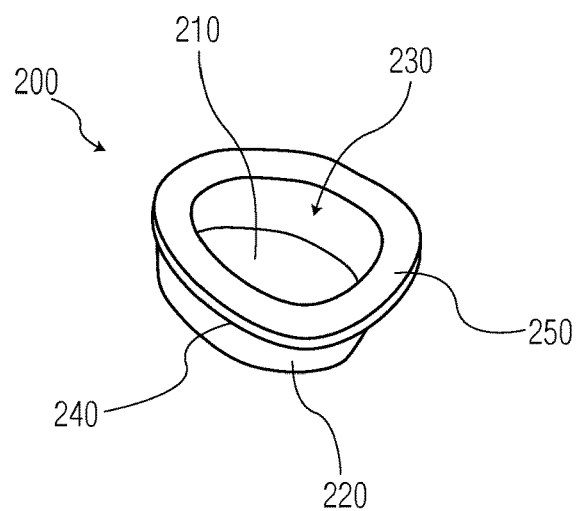
FIG. 12 is an oblique perspective view of an inner surface of the earcup.

In an embodiment of FIGS. 10 and 11, the earcup 200 includes a base 210, a sidewall 220, an ear receiving space 230, a flange 240, and a gasket 250. The earcups 200 are made of a dense polymer, such as polycarbonate, acrylic, ABS, epoxy resin, polyurethane, and silicone, although one of ordinary skill in the art would appreciate that other dense plastics, and sound attenuating materials may also be used. The base 210 is substantially planar, having a general circular or oval-shape and an outer circumferential peripheral edge. In an embodiment, the base 210 is contoured, having a generally convex surface extending outward from the peripheral edge.

In an embodiment, the earcup 200 is optically transparent, enabling areas in and around the ear to be easily examined for evidence of skin breakdown or superficial edema as indicated by a change in color, swelling, bleeding or exudates, without removal of the earcup. In an embodiment, the earcup 200 is optically translucent. In an embodiment, the earcup 200 is optically opaque.

In an embodiment, the base 210 has a thickness of approximately 0.03 inch (0.8 mm) to 0.13 inch (3.2 mm) thick. In another embodiment, the base 210 has a thickness of approximately 0.03 inch (0.8 mm) to 0.08 inch (2.03 mm). In another embodiment, the base 210 has a thickness of approximately 0.06 inch (1.6 mm). The sidewall 220 extends approximately orthogonally from the base 210, having a first sidewall edge 210a continuously connected along the length of the peripheral edge of the base 210, and an opposite second sidewall edge 210b. In an embodiment, the first sidewall edge 210a extends approximately in the same plane as the base 210. In an embodiment, the second sidewall edge 210b is contoured, having a cross-sectional half having a peak on each opposing end and valley disposed therebetween, as seen in the embodiment of FIG. 11.

Taken together, the base 210 and the continuous sidewall 220 form the ear receiving space 230. One of ordinary skill in the art would appreciate that the dimensions of the base 210 and sidewall 220 may be varied to increase or decrease a volume of the ear receiving space 230.

The flange 240 extends radially from a second sidewall edge, having an inner flange contact surface 240b extending orthogonally outward from the second sidewall edge, and an opposite outer flange surface 240a. As seen in the embodiment of FIG. 11, the inner flange contact surface 240b is contoured and complementary to that of the second sidewall edge 210b, having a cross-sectional half with a peak on each opposing end and a valley disposed therebetween. The contoured surface of the flange 240 is complementary to the natural curvature of a head of the newborn, allowing a flange contact surface (not labeled) to form a continuous seal along an entire circumference of the flange 240.

Figure 9:
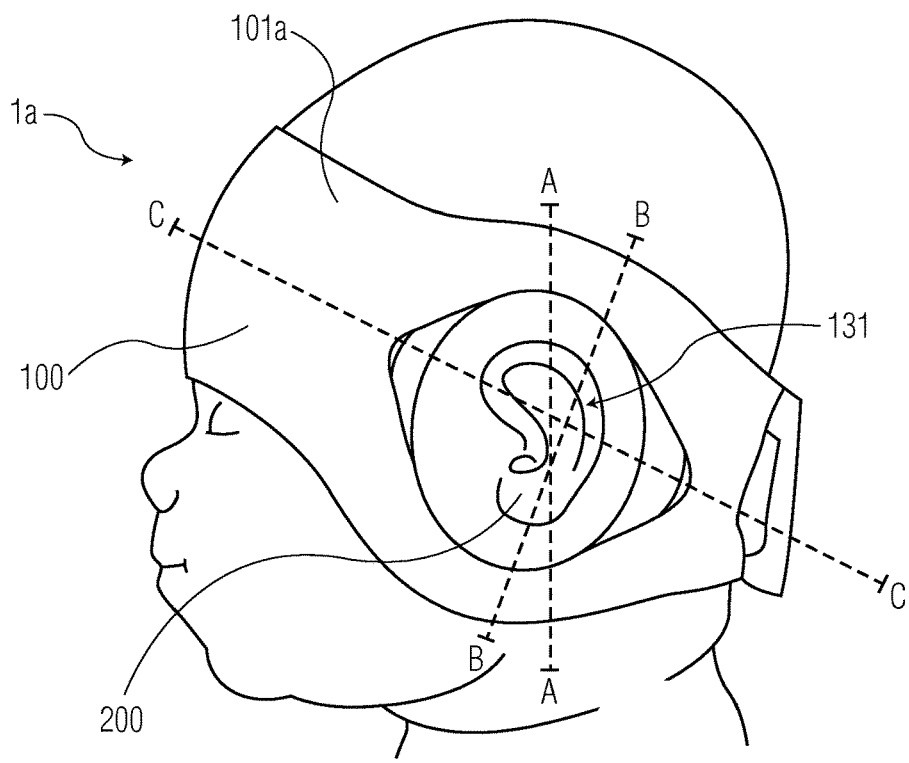
FIG. 9 is a perspective view of a left side of the rear-closing medical headgear positioned on the head of the preterm newborn, and having an earcup.

In the embodiments of FIGS. 9 and 10, a longitudinal axis A extends lengthwise along the earcup 200. A headgear circumferential axis C corresponds to a longitudinal axis of the medical headgear 1 when the earcup 200 is positioned in the earcup receiving space 121,131. A contoured axis B extends substantially orthogonal to the circumferential axis C. The first sidewall edge 210a and/or the inner flange contact surface 240b are generally contoured along opposite edges of the earcup 200 intersecting with the contoured axis B. The contoured first sidewall edge 210a and/or inner flange contact surface 240b have a shape complimentary to the contoured shape of the head of a newborn. In an embodiment, the first sidewall edge 210a and/or inner flange contact surface 240b of the earcup 200 is asymmetrical along the longitudinal axis A.

Figure 2:
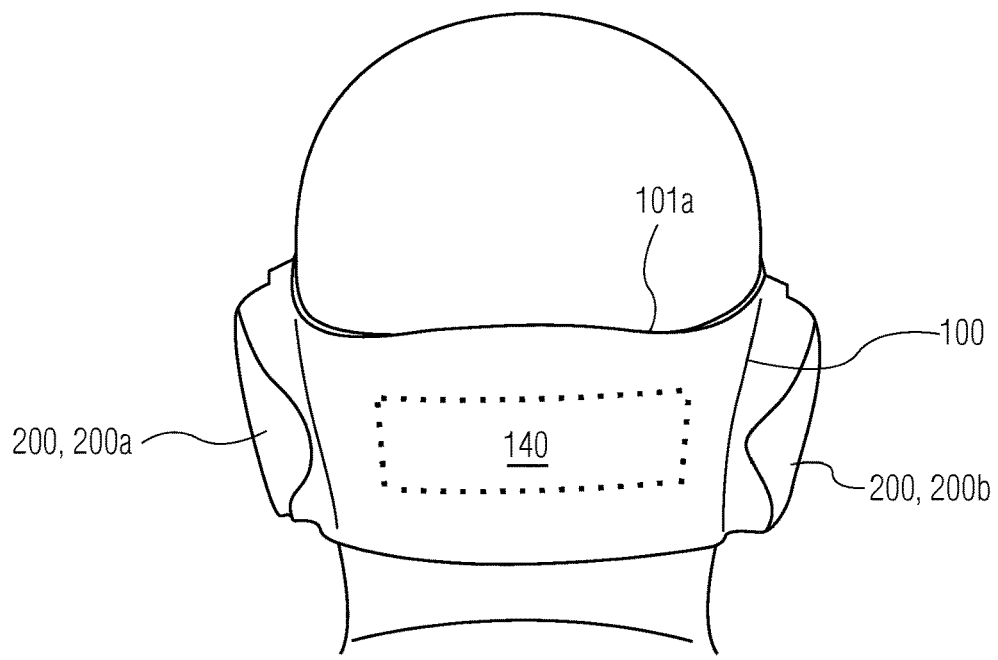
FIG. 2 is a rear perspective view of a rear-closing medical headgear.

In an embodiment of FIG. 2, the earcup 200 is a left-sided earcup 200a having a contoured first sidewall edge 210a and/or inner flange contact surface 240b complimentary to the contoured shape of the head of a newborn surrounding the left ear of the newborn. In an embodiment of FIG. 2, the earcup 200 is a right-sided earcup 200b having a contoured first sidewall edge 210a and/or inner flange contact surface 240b complimentary to the contoured shape of the head of a newborn surrounding the right ear of the newborn. The left-sided earcup 200a is a non-superimposable mirror image of the right-sided earcup 200b, such that the earcups 200a,200b are chiral with respect to each other.

Figure 13:
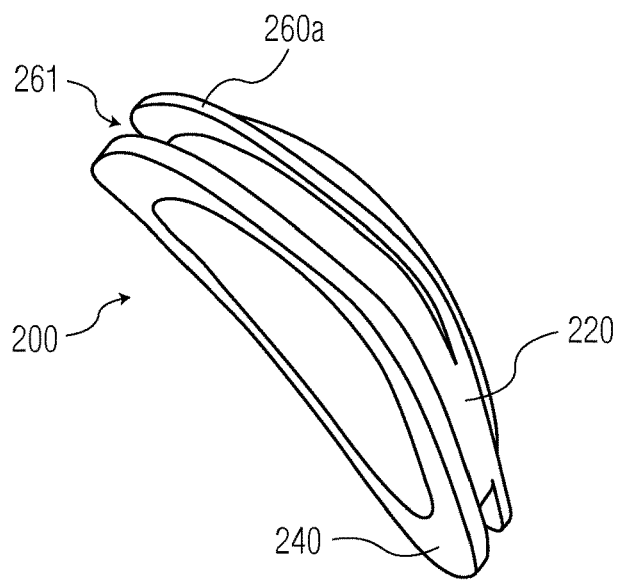
FIG. 13 is a lower oblique perspective view of the earcup having a first outer retaining flange.
Figure 14:
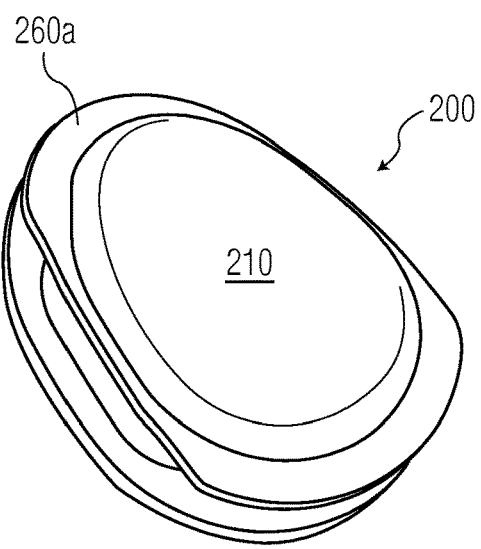
FIG. 14 is an upper oblique perspective view of the earcup in FIG. 13.

In the embodiments of FIGS. 13 and 14, the earcup 200 further includes a first retaining flange 260a disposed continuously and circumferentially on the continuous sidewall 220, between the base 210 and the flange 240. The first retaining flange 260a radially extends outward from the outer surface of the continuous sidewall 200. Taken together, the first retaining flange 260a, the continuous sidewall 200, and the flange 240 form a circumferentially extending band receiving space 261.

Figure 15:
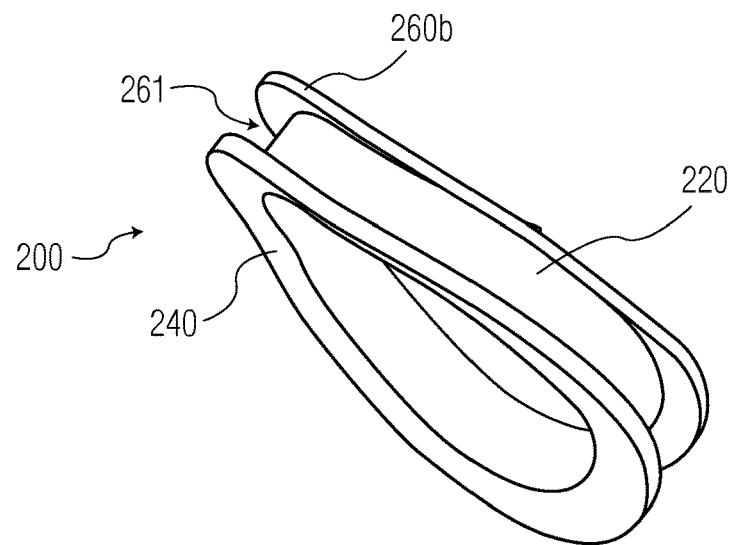
FIG. 15 is a lower oblique perspective view of the earcup having a second outer retaining flange.
Figure 16:
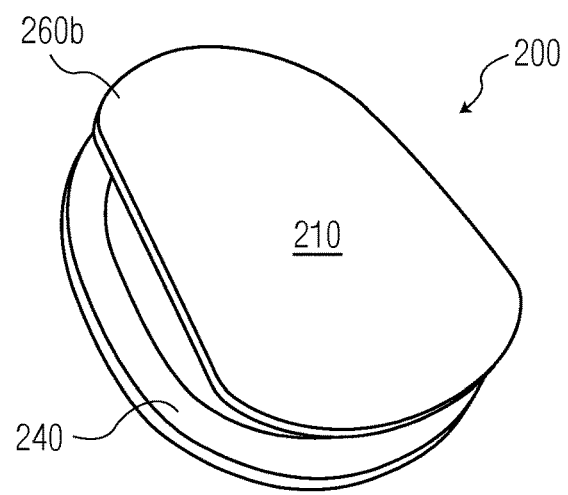
FIG. 16 is an upper oblique perspective view of the earcup in FIG. 15.

In the embodiments of FIGS. 15 and 16, the earcup 200 further includes a second retaining flange 260b disposed continuously and circumferentially on the substantially planar base 210. The second retaining flange 260b radially extends outward from the peripheral edge of the base 210, in approximately the same plane as the surface of the base 210. Taken together, the second retaining flange 260b, the continuous sidewall 200, and the flange 240 form the circumferentially extending band receiving space 261. The gasket 250 is positioned on the flange contact surface of the flange 240, extending continuously along the circumference of the flange contact surface. In an embodiment, the gasket 250 is connected to the flange 240 through an adhesive. The gasket 250 may be made of open or closed-cell foam, such as open-cell urethane foam, or silicone foam. In an embodiment, the gasket 250 is made of an open-cell foam that is breathable, whereby moisture may be able to pass therebetween.

In an embodiment, the gasket 250 has a thickness of 1-6 mm. In an embodiment, the gasket 250 has a thickness of 1-4 mm. In an embodiment, the gasket 250 has a thickness of 2-4 mm. In another embodiment, the gasket 250 has a thickness of 3-6 mm. In an embodiment, the gasket 250 has a compression force range for 25% deflection of 0.25-8 psi. In another embodiment, the gasket 250 has a compression force range for 25% deflection of 0.3-3.5 psi.

In an embodiment, when the earcup 200 is made from a flexible material such as silicone rubber, the use of the gasket 250 is optional. When the earcup 200 is used in the absence of the gasket 250, the flange 240 is optionally flexible, allowing the flange 240 to resiliently conform to the contours of a user's head.

In the embodiments of FIGS. 1-8, the plurality of medical device fasteners 300 are positioned on the outer surface 101a of the band 100. In an embodiment, one, two, three, four, or more medical device fasteners 300 are positioned on the outer surface 101a.

Figure 5:
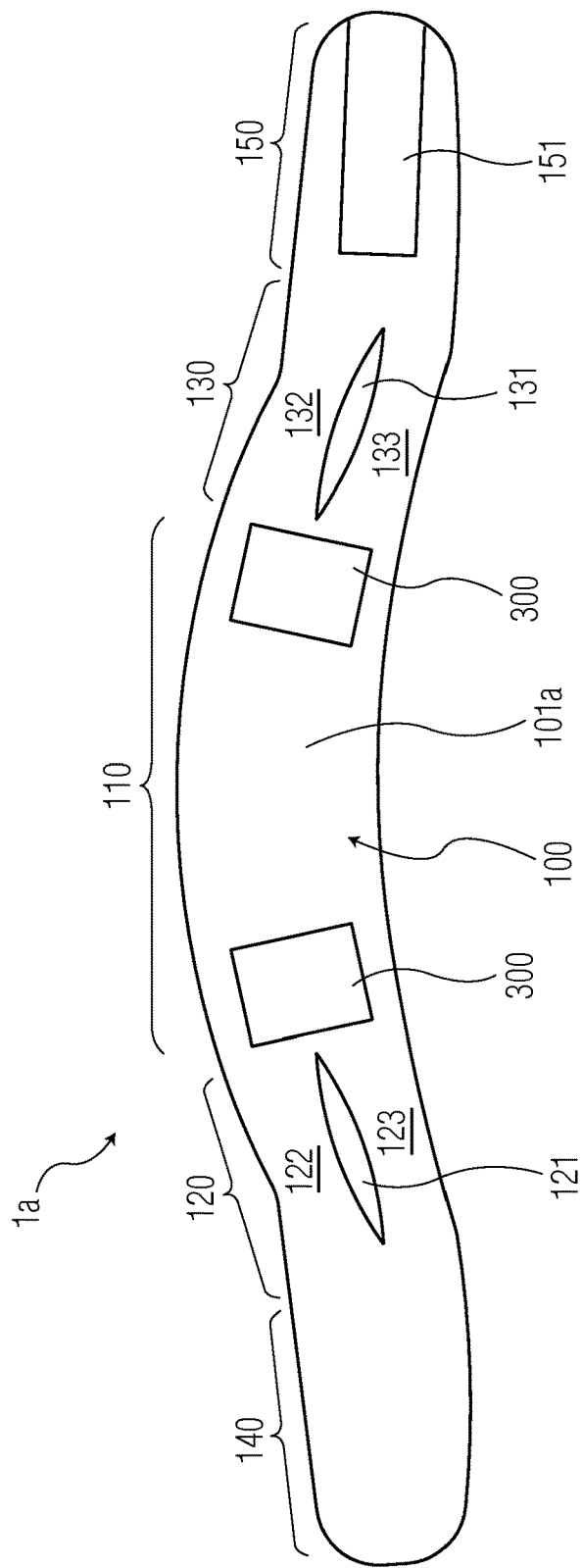
FIG. 5 is a perspective view of an outer facing side of a rear-closing medical headgear.

In the rear-closing embodiments 1a of FIGS. 1 and 5, a pair of medical device fasteners 300 is positioned on the outer surface 101a of the non-stretch central portion 110, with one medical device fastener 300 positioned proximate to the first side, and one medical device fastener 300 positioned proximate to the second side. In another rear-closing embodiment 1a, a third medical device fastener 300 is positioned on an approximate mid-portion of the non-stretch central portion 110.

Figure 3:
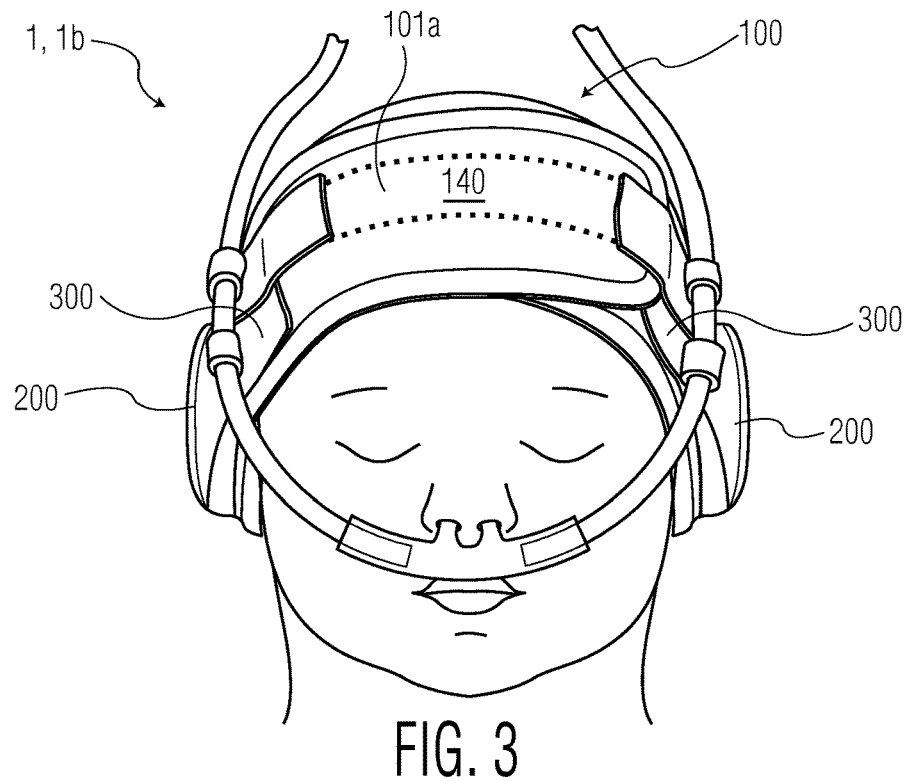
FIG. 3 is a front perspective view of a front-closing medical headgear installed on a head of a preterm newborn.
Figure 4:
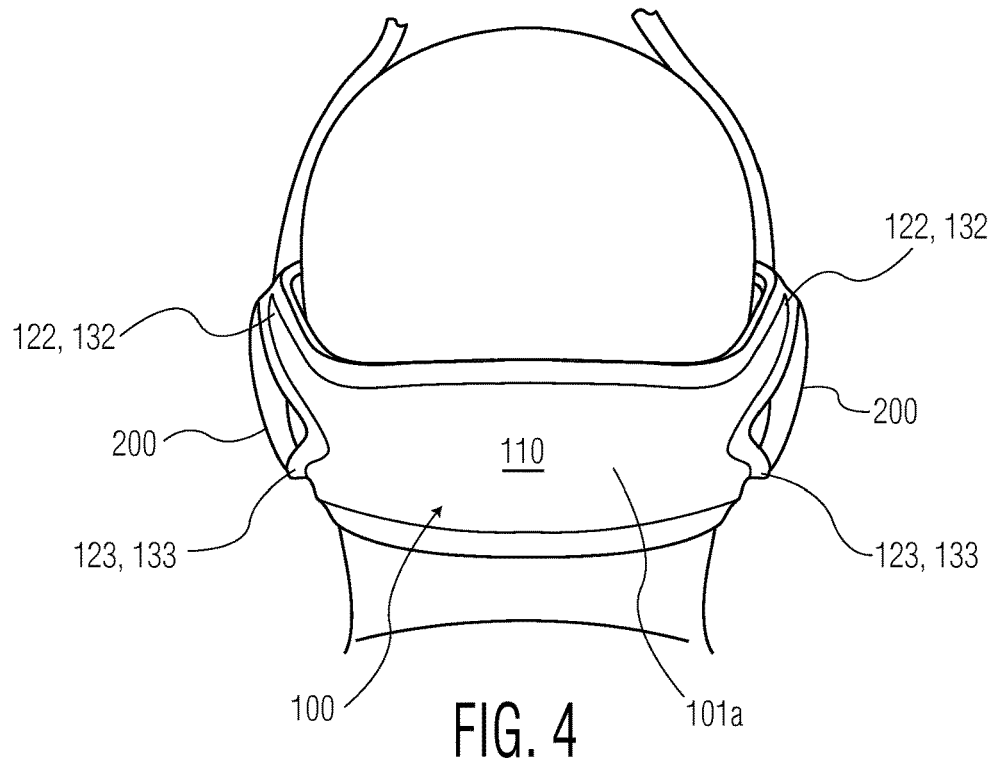
FIG. 4 is a rear perspective view of a front-closing medical headgear.
Figure 7:
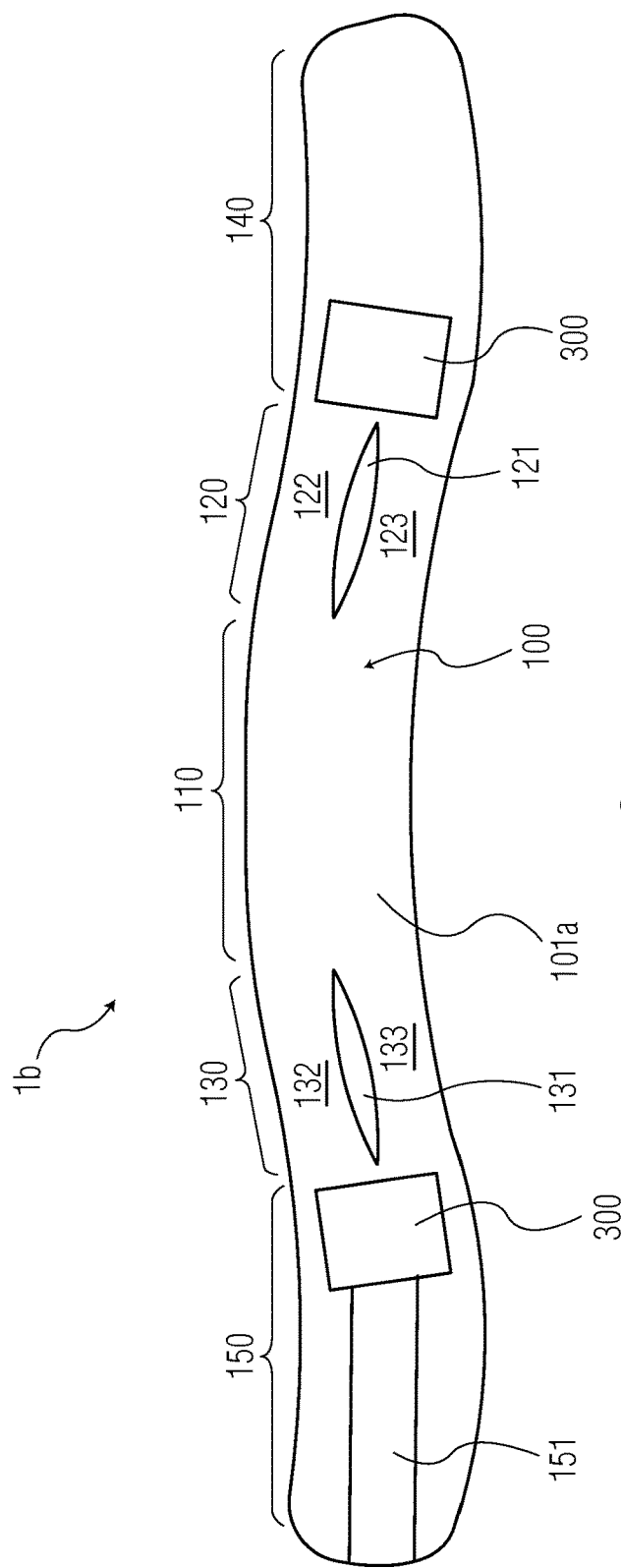
FIG. 7 is a perspective view of an outer facing side of a front-closing medical headgear.

In the front-closing embodiments 1b of FIGS. 3 and 7, the pair of medical device fasteners 300 is positioned on the outer surface 101a of the non-stretch terminating end portions 140,150. Specifically, one medical device fastener 300 is positioned proximate to the elastic portion connecting side of the first terminating end portion 140, and one medical device fastener 300 is positioned proximate to the elastic portion connecting side of the second terminating end portion 150. In another front-closing embodiment 1b, a third medical device fastener 300 is positioned on an approximate mid-portion of the outer surface 101b of the first or second terminating end portions 140.

In an embodiment, a removable eyeshade (not shown) may be connected to the band 100 to modify or control the visual environment of a user newborn. The eyeshade may be connected by a hook and loop fastener or any other suitable fastening mechanism known to those of ordinary skill in the art. In an embodiment, the eyeshade is substantially similar to the removable eyeshade described in U.S. Pat. No. 7,878,968 issued to Wittmann-Price et al., with col. 3, lines 52-67 through col. 4, lines 1-8 incorporated herein by reference.

Assembly of the major components and the operation of the medical headgear 1 will now be described.

Each earcup 200 is positioned in the first and second earcup receiving spaces 121,131 by inserting the base 210 and the sidewall 220 through the earcup receiving spaces 121,131 from the inner surface 101b towards the outer surface 101a of the band 100. As the earcup 200 is positioned in the first earcup receiving space 121, the upper strap 122 and lower strap 123 are elastically displaced, exerting opposing elastic forces against the sidewall 220 to secure the earcup 200 in the first earcup receiving space 121. Similarly, the earcup 200 is positioned in the second earcup receiving space 131.

In the embodiments of FIGS. 13-17, when the earcup 200 is positioned in the first or second earcup receiving spaces 121,131 a portion of the upper straps 122,132 and lower straps 123,133 defining the first and second earcup receiving spaces 121,131 are received in the band receiving space 261.

When the earcup 200 is positioned in the earcup receiving spaces 121,131, the outer flange surface 240a contacts the inner surface 101b of the band 100, preventing the earcup 200 from being displaced out of an outer surface side of the earcup receiving spaces 121,131 when an outward force is applied to the earcup 200.

Figure 17:
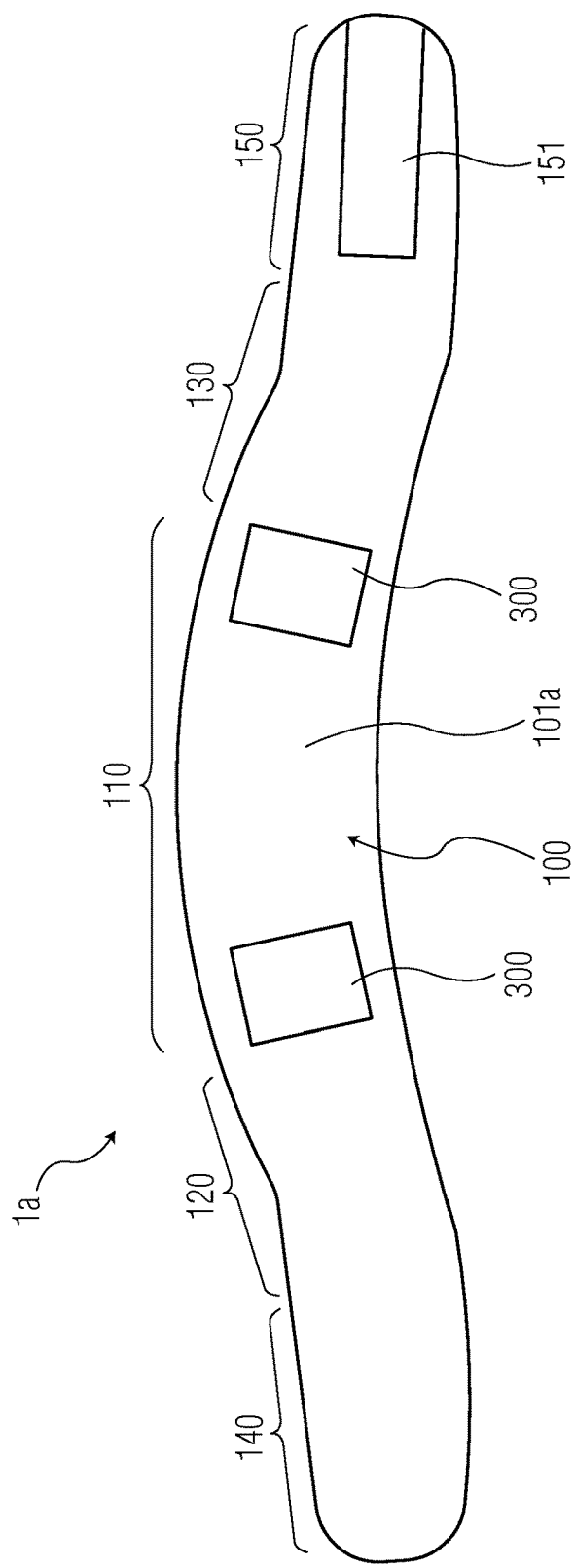
FIG. 17 is a perspective view of an outer facing side of a rear-closing medical headgear.

In the embodiment of FIG. 17, where the first elastic portion 120 and second elastic portion 130 extend continuously as unbifurcated portions of fabric, the outer surface of the ear cup 200 base 210 is positioned against the inner surface 101b of the first or second elastic portions 120,130. When an inward force is applied by the band 100, the outer surface of the base 210 contacts the inner surface 101b, preventing the earcup 200 from being displaced when an outward force is applied to the earcup 200.

In the rear-closing embodiments 1a of FIGS. 1, 2, 5, and 6, the inner surface 101b and first friction pad 111a of the non-stretch central portion 110 are positioned against the forehead, or higher on the frontal cranial bones anterior to the anterior fontanelle of a newborn. The earcups 200 in the first and second earcup receiving spaces 121,131 are positioned over the ears of the newborn, such that the ears extend into the ear receiving space 230. The upper and lower straps 122,132/123,133 of the first and second elastic portions 120,130 flank upper and lower portions of the ear, applying opposing inward elastic forces on the outer flange surface 240a, driving the inner flange surface 240b towards the head, compressing the gasket 250, and ultimately forming a seal between the earcups 200 and the head of the newborn.

In an embodiment (not shown, but discussed above), the inner surface 101b of the first non-stretch terminating end portion 140 is positioned against a nape of the neck, around a base of the head. In an embodiment, the friction pad positioned on the inner surface 101b of the first non-stretch terminating end portion 140 also contacts the nape of the neck. The second fastener 151 on the inner surface 101b of the second non-stretch terminating end portion 150 is positioned over the outer surface 101a of the first non-stretch terminating end portion 140, such that the second fastener 151 contacts and detachably engages the first fastener 141 on the outer surface 101b of the first non-stretch terminating end portion 140.

In an embodiment of FIG. 6, the inner surface 101b of the second non-stretch terminating end portion 150 is positioned against the nape of the neck, around the base of the head. Optionally, the friction pad may be positioned on the inner surface 101b and also contacts the nape of the neck. The first fastener 141 and the inner surface 101b of the first non-stretch terminating end portion 140 are positioned over the outer surface 101b of the second non-stretch terminating end portion 150, such that the first fastener 141 contacts and detachably engages the second fastener on the outer surface 101b of the second non-stretch terminating end portion 150.

In the front-closing embodiments 1b of FIGS. 3, 4, 7, and 8, the inner surface 101b and first friction pad 111a of the non-stretch central portion 110 are positioned against the nape of the neck, around the base of the head. The earcups 200 in the first and second earcup receiving spaces 121,131 are positioned over the ears of the newborn, such that the ears extend into the ear receiving space 230. The upper and lower straps 122,132/123,133 of the first and second elastic portions 120,130 flank upper and lower portions of the ear, applying opposing inward elastic forces on the outer flange surface 240a, driving the inner flange surface 240b towards the head, compressing the gasket 250, and ultimately forming a seal between the earcups 200 and the head of the newborn.

Figure 8:
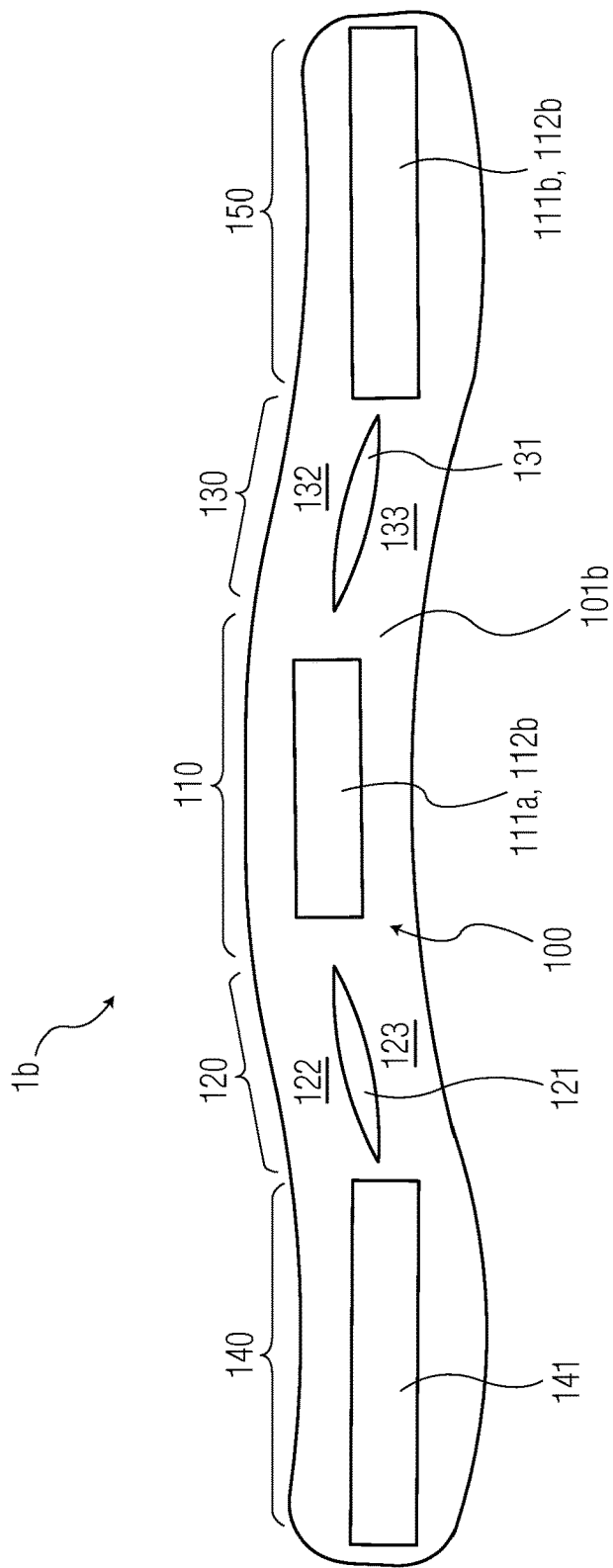
FIG. 8 is a perspective view of an inner facing side of the front-closing medical headgear.

In an embodiment of FIG. 8, the inner surface 101b and the second friction pad 111b of the second non-stretch terminating end portion 150 are positioned against the forehead, or higher on the frontal cranial bones anterior to the anterior fontanelle. The first fastener 141 on the inner surface 101b of the first non-stretch terminating end portion 140 is positioned over the outer surface 101a of the second non-stretch terminating end portion 150, such that the first fastener 141 contacts and detachably engages the second fastener 151 on the outer surface 101b of the second non-stretch terminating end portion 150.

In an embodiment (not shown but discussed above), the inner surface 101b and the friction pad of the first non-stretch terminating end portion 140 are positioned against the forehead, or higher on the frontal cranial bones anterior to the anterior fontanelle. The second fastener 151 on the inner surface 101b of the second non-stretch terminating end portion 150 is positioned over the outer surface 101a of the first non-stretch terminating end portion 140, such that the second fastener 151 contacts and detachably engages the first fastener 141 on the outer surface 101b of the first non-stretch terminating end portion 140.

A compressive force generated by the medical headgear 1 against the head is distributed across the non-stretch central portion 110, first non-stretch terminating end portion 140, and second non-stretch terminating end portion 150. Since the first and second elastic portions 120,130 are the sole elastic portions on the medical headgear 1, a compressive force may be generated directly over to the earcups 200 through a circumferential tensile force applied across the band 100. The compressive force is therefore specifically isolated against the earcup 200, contributing to the formation of the seal between the earcup 200 and the head, while being generally dispersed over the larger area of the non-stretch portions 110,140,150.

In an embodiment, the bifurcated medical headgear 1 is optionally used in the absence of the earcups 200. When the bifurcated headgear 1 is positioned on the head of the newborn, as described above, each ear of the newborn is positioned in the first or second earcup receiving spaces 121,131, extending outward therethrough.

In an embodiment of FIG. 17, where the first elastic portion 120 and the second elastic portion 130 extend continuously as unbifurcated portions of fabric, the medical headgear 1 is optionally used in the absence of the earcups 200. When the unbifurcated headgear 1 is positioned on the head of a newborn, as described above, the inner surfaces 101b of the first or second elastic portions 120,130 are positioned directly against the ears of a newborn in the absence of the earcups 200. Additionally, when the unbifurcated medical headgear 1 is positioned on the head of a newborn, as described above, the inner surfaces 101b of the first or second elastic portion 120,130 are positioned against the head, above the ears of the newborn in the absence of the earcups 200.

The above described embodiments of the medical headgear 1 are suitable for use on preterm newborns, reduce environmental noise to in-utero acoustic levels, and provide a stable support for attaching respiratory support tubes and other medical devices.

For both rear-closing embodiments 1a of FIGS. 1, 2, 5, and 6, and front-closing embodiments 1b of FIGS. 3, 4, 7, and 8, the band 100 may be positioned on the head such that the anterior and posterior fontanelles of the newborn are exposed, enabling the fontanelles to be easily examined, for example to inspect the anterior fontanelle for evidence of intraventricular hemorrhage.

While the above embodiments are written in the context of newborns, and more specifically, towards preterm newborns, the medical headgear 1 is not limited to such an application. Rather, one of ordinary skill in the art would appreciate that the scale of the medical headgear 1 can be increased for application in adolescents and adults, without departing from the scope and spirit of the invention.

Additionally, the medical headgear 1 may optionally be used without the earcups 200. Without the earcups 200, the medical headgear 1 may serve as a securing device for attachment of respiratory support tubes or other medical equipment.

While the invention has been described in detail and with reference to specific embodiments, one of ordinary skill in the art would appreciate that the described embodiments are illustrative, and that various changes and modifications can be made without departing from the scope of the invention.

What is claimed is:

1. A medical headgear comprising:
   a flexible band having
      an inner surface,
      an opposite outer surface,
      a non-stretch central portion having a first side and an opposite second side, a first elastic portion connected to the first side, and a second elastic portion connected to the second side, wherein an area of the flexible band as a whole between the first elastic portion and the second elastic portion stretches less than the first elastic portion and the second elastic portion, the first and second elastic portions are bifurcated, each having an upper strap and a corresponding lower strap extending approximately along a longitudinal axis and defining an earcup receiving space therebetween; and an earcup positioned in each earcup receiving space, the earcup is a frequency-dependent auditory filter providing sound attenuation generally increasing as a function of frequency.

2. The medical headgear of claim 1, wherein the flexible band further comprises a first terminating end portion connected to the first elastic portion.

3. The medical headgear of claim 2, wherein the first terminating end portion is formed to be non-stretching.

4. The medical headgear of claim 3, wherein the flexible band further comprises a second terminating end portion connected to the second elastic portion and formed to be non-stretching.

5. The medical headgear of claim 2, wherein the first terminating end portion is formed to have an elastic first part, and a non-stretch second part.

6. The medical headgear of claim 2, wherein the flexible band further comprises a first fastener positioned on a surface the first terminating end portion.

7. The medical headgear of claim 6, wherein the flexible band further comprises a first friction pad positioned on an inner surface of the first terminating end portion when the first fastener is positioned on an outer surface.

8. The medical headgear of claim 6, wherein the flexible band further comprises a second terminating end portion connected to the second elastic portion.

9. The medical headgear of claim 8, wherein the flexible band further comprises a second fastener complimentary to the first fastener, and positioned on a surface of the second terminating end portion opposite to that of the first fastener.

10. The medical headgear of claim 8, wherein the second terminating end portion is formed to be non-stretching.

11. The medical headgear of claim 8, wherein the second terminating end portion is formed to have an elastic first part, and a non-stretch second part.

12. The medical headgear of claim 1, wherein the upper and lower straps are elastically displaced by the earcup, and exert opposing elastic forces against the earcup to secure the earcup in the earcup receiving space.

13. The medical headgear of claim 12, wherein the earcup is held in the earcup receiving space only by the opposing elastic forces of the upper strap and the lower strap.

14. The medical headgear of claim 13, wherein the opposing elastic forces extend along a direction perpendicular to the longitudinal axis.

15. The medical headgear of claim 1, wherein the earcup provides at least 12 dBA in sound reduction.

16. The medical headgear of claim 1, wherein the earcup provides at least an 8 dB noise reduction rating (NRR).

17. The medical headgear of claim 1, wherein the frequency-dependent auditory filter attenuates sounds between 300-500 Hz.

18. The medical headgear of claim 1, wherein the frequency-dependent auditory filter substantially blocks sounds above 2000 Hz.

19. The medical headgear of claim 1, wherein the earcup comprises:

a base, a sidewall having a first sidewall edge continuously connected along a peripheral edge of the base, extending approximately orthogonally from the base, and an opposite second sidewall edge;

an ear receiving space formed from the base and sidewall; and a flange extending radially from the second sidewall edge and having a contoured inner flange contact surface with a cross-sectional half having a peak on each of a pair of opposing ends and a valley disposed therebetween.

20. The medical headgear of claim 19, further comprising a gasket positioned on the contoured inner flange contact surface and having a thickness of 1-6 mm.

21. The medical headgear of claim 20, wherein the gasket has a compression force range for 25% deflection of 0.3-8 psi.

22. The medical headgear of claim 19, wherein the earcup includes a retaining flange extending radially from the sidewall and forming a circumferentially extending band receiving space defined by the retaining flange, the flange, and the sidewall.

23. The medical headgear of claim 22, wherein the upper strap and the lower strap are positioned in the band receiving space.

24. The medical headgear of claim 1, wherein an applied circumferential tensile force across the band is specifically isolated against the earcups.

25. The medical headgear of claim 1, wherein the band further comprises one or more medical device fasteners positioned on an outer surface.

26. The medical headgear of claim 1, further comprising an eyeshade connected to the band.

27. The medical headgear of claim 1, wherein the first and the second elastic portions extend continuously from the first and the second sides of the non-stretch central portion.

28. The medical headgear of claim 1, wherein the earcup is optically transparent, translucent, or opaque.

29. The medical headgear of claim 1, wherein the earcup is a frequency-dependent auditory filter providing sound attenuation that approximates the sound attenuation characteristics of a mother's gravid uterus and abdominal cavity.

30. The medical headgear of claim 1, wherein a width of the upper strap is different than a width of the lower strap.

31. The medical headgear of claim 1, wherein the earcup is removably positioned in the earcup receiving space and rotatable within the earcup receiving space.

32. The medical headgear of claim 1, wherein the area of the flexible band as a whole between the first elastic portion and the second elastic portion stretches less than the first elastic portion and the second elastic portion from a relaxed state of the flexible band.

33. A medical headgear comprising:

a flexible band formed of an elastic material and having an inner surface configured to face a user, an opposite outer surface, a non-stretch central portion having a first side and an opposite second side, the non-stretch central portion including a layer of silicone rubber adhered to the inner surface of the flexible band and limiting stretching of the flexible band in the non-stretch central portion, a first elastic portion connected to the first side, and a second elastic portion connected to the second side.

34. The medical headgear of claim 33, wherein the layer of silicone rubber forms a friction pad positioned in the non-stretch central portion on the inner surface.

35. A medical headgear comprising:
a flexible band having
an inner surface,
an opposite outer surface,
a non-stretch central portion having a first side and an opposite second side,
a first elastic portion connected to the first side, and
a second elastic portion connected to the second side, wherein an area of the flexible band as a whole between the first elastic portion and the second elastic portion stretches less than the first elastic portion and the second elastic portion, the first and second elastic portions are bifurcated, each having an upper strap and a corresponding lower strap extending approximately along a longitudinal axis, connected at opposite ends, and defining an earcup receiving space therebetween; and
an earcup positioned in each earcup receiving space, the earcup includes a base and a sidewall continuously connected along a peripheral edge of the base and extending approximately orthogonally from the base, the upper and lower straps are elastically displaced by the sidewall and exert opposing elastic forces against the sidewall to secure the earcup in the earcup receiving space, the earcup is removably and rotatably held in the earcup receiving space only by the opposing elastic forces of the upper strap and the lower strap.

36. The medical headgear of claim 35, wherein the sidewall has a first sidewall edge continuously connected along the peripheral edge of the base and an opposite second sidewall edge, the earcup includes an ear receiving space formed from the base and sidewall and a flange extending radially from the second sidewall edge.

37. The medical headgear of claim 36, wherein the earcup includes a retaining flange extending radially from the sidewall and forming a circumferentially extending band receiving space defined by the retaining flange, the flange, and the sidewall.

38. The medical headgear of claim 37, wherein the upper strap and the lower strap are positioned in the band receiving space.

* * * * *